United States Patent [19]
Lefort et al.

[11] 3,980,686
[45] Sept. 14, 1976

[54] PROCESS FOR THE PREPARATION OF CHLOROSILANE

[75] Inventors: Marcel Lefort, Caluire; Gilbert Marin, Sainte-Foy-les-Lyon, both of France

[73] Assignee: Rhone-Poulenc Industries, Paris, France

[22] Filed: July 23, 1975

[21] Appl. No.: 598,268

[30] Foreign Application Priority Data

July 26, 1974 France .............................. 74.26083

[52] U.S. Cl. ......................................... 260/448.2 P
[51] Int. Cl.² ............................................ C07F 7/12
[58] Field of Search ................ 260/448.2 P, 448.2 E

[56] References Cited
UNITED STATES PATENTS

| | | | |
|---|---|---|---|
| 2,887,500 | 5/1959 | McEntee | 260/448.2 P |
| 2,900,225 | 8/1959 | Clasen | 260/448.2 P X |
| 3,044,845 | 7/1962 | Jex et al. | 260/448.2 P X |
| 3,655,710 | 4/1972 | Bazouin et al. | 260/448.2 P |

*Primary Examiner*—Paul F. Shaver
*Attorney, Agent, or Firm*—Stevens, Davis, Miller & Mosher

[57] ABSTRACT

Dichlorosilane and phenyltrichlorosilane are prepared in good yields by reacting trichlorosilane and diphenyldichlorosilane in the presence of aluminium chloride, as catalyst, and a small proportion of a cocatalyst which is selected from hydrochloric acid and alumina and mixtures thereof, isolating the dichlorosilane from the reaction medium as it is formed and isolating the phenyltrichlorosilane obtained at the end of the reaction.

9 Claims, No Drawings

PROCESS FOR THE PREPARATION OF CHLOROSILANE

The present invention relates to a process for the preparation of chlorosilanes, in particular dichlorosilane and phenyltrichlorosilane by means of a rearrangement reaction between trichlorosilane and diphenyldichlorosilane.

It is known that it is possible to convert hydrogenosilanes into other hydrogenosilanes by redistribution or disproportionation reactions. Thus, compounds such as methyldichlorosilane have been obtained from trichlorosilane and trimethylchlorosilane. Such rearrangements are described in U.S. Pat. No. 2,647,912 and in Japanese Patents Nos. 23,171 (1961) and 23,172 (1961) as well as in Chemical Abstracts, 53, 21,747. Dichlorosilane has also been prepared by disproportionation of trichlorosilane, in the presence of various catalysts. These disproportionation processes, which utilize aluminium chloride, nitriles, cyanamides, tertiary amines or quaternary ammonium compounds as the catalyst, are described in, for example, U.S. Pat. Nos. 2,735,861, 2,732,280, 2,732,281 and 2,732,282 and in French Patent Nos. 985,985 and 2,096,605. When these diverse processes are used, the same number of mols of dichlorosilane as of silicon tetrachloride are produced. The production of large amounts of silicon tetrachloride, the use for which is very restricted, is undoubtedly a disadvantage.

A process for the preparation of dichlorosilane and phenyltrichlorosilane has now been found, and it is this which forms the subject of the present invention. According to the process of this invention trichlorosilane and diphenyldichlorosilane are reacted in the presence of aluminium chloride, as catalyst, and in the presence of a small proportion of a co-catalyst chosen from hydrochloric acid and/or alumina, and the dichlorosilane formed is isolated from the reaction medium as it is formed, and the phenyltrichlorosilane obtained is isolated at the end of the reaction.

The catalyst consists of aluminium chloride containing a small proportion of a co-catalyst. When the co-catalyst is hydrochloric acid, the amount of hydrochloric acid, expressed by weight, is usually at most equal to 30% and preferably 0.1 to 10% of the weight of aluminium chloride employed. The hydrochloric acid can be introduced directly, for example by bubbling in hydrogen chloride in the gaseous state, or can be introduced by adding water since the water, reacting with anhydrous aluminium chloride, liberates hydrochloric acid. It is also possible to achieve the desired hydrochloric acid content by suitably exposing anhydrous aluminium chloride to a moisture-containing atmosphere. It is also possible to introduce into the reaction medium any compound capable of yielding water which will react with the aluminium chloride.

Alumina, which can also be used as the co-catalyst, is added in such a way that it generally represents, in terms of weight, at most 20% of the total weight of chlorosilanes. The preferred proportion is 0.01 to 5% of the weight of chlorosilanes. The alumina can be anhydrous or hydrated and can have a high or low specific surface area. The use of a hydrated alumina implies that alumina and hydrochloric acid are used simultaneously as the co-catalyst.

The aluminium chloride is suitably used in an amount, by weight, from 0.1 to 10%, preferably from 0.5 to 5%, relative to the weight of chlorosilanes introduced.

The proportions of the reagents are not critical. 2 to 5 mols of hydrogenosilane per mol of diphenyldichlorosilane are preferably used so as to convert the diphenyldichlorosilane completely.

The temperature at which the reaction is carried out is generally from 30° to 200°C, and preferably from 50° to 120°C. The dichlorosilane is removed continuously throughout the duration of the reaction. This removal process is advantageously effected by carrying out the reaction under reflux and by distilling and isolating the dichlorosilane as it is formed.

The process is generally carried out under atmospheric pressure; it can, however, be carried out under lower or higher pressures. For a particular pressure, the reflux temperature can be controlled by adjusting the composition of the mixture. Thus, all the reagents can be introduced initially. It is also possible to introduce the trichlorosilane gradually during the reaction; this makes it possible to work at a higher reflux temperature.

The process according to the invention makes it possible to obtain dichlorosilane in 80% yields relative to the trichlorosilane employed. Dichlorosilane is of undoubted industrial value since it makes it possible to produce coatings of pure silicon, after decomposition at a high temperature (epitaxy of silicon). Pure silicon deposits are particularly desired in the semiconductor field. The process according to the invention, which can be carried out at a relatively moderate temperature, also makes it possible to obtain phenyltrichlorosilane. This compound is valuable in the preparation of organosilicon resins used, for example, as adhesives or for insulating electrical conductors.

The following Examples further illustrate the present invention.

EXAMPLE 1

253 g of diphenyldichlorosilane and 10 g of aluminium chloride containing 4% by weight of hydrochloric acid are introduced into a flask. (The hydrochloric acid was introduced by adding 0.2 g of water to the aluminium chloride.) The mixture is heated to 100°C and 314 g of trichlorosilane are run in over the course of 6 hours; the temperature is kept at 100°C during the whole of the experiment, whilst the vapours escaping from the flask are distilled in such a way as to isolate dichlorosilane at the top of the column and to recycle to the flask the products with a boiling point higher than that of dichlorosilane. (B.p.$_{760}$: 8.3°C). A distillate weighing 55 g, containing 46 g of dichlorosilane and 9 g of trichlorosilane, is thus obtained. 460.5 g of a mixture consisting, according to chromatographic analysis data, of 20.5% of trichlorosilane, 57.4% of phenyltrichlorosilane and 14.9% of diphenyldichlorosilane, remain in the flask. 44 g of dichlorosilane are isolated by rectification. The yield of dichlorosilane produced relative to the trichlorosilane converted is 69.2%. 260 g of phenyltrichlorosilane are isolated on distilling the mixture remaining in the flask.

EXAMPLE 2

253 g of diphenyldichlorosilane and 25 g of aluminium chloride containing 4% of hydrochloric acid are introduced into a flask; 384.5 g of trichlorosilane are run in over the course of 7 hours, whilst keeping the reaction mixture at 70°C and distilling the dichlorosilane. A fraction weighing 56.3 g, containing 98.3% of dichlorosilane, is obtained. 525 g of a mixture containing 76% of phenyltrichlorosilane remain in the flask.

EXAMPLE 3

253 g of diphenyldichlorosilane and 40 g of aluminium chloride containing 4% of hydrochloric acid are introduced into the flask; 401.5 g of trichlorosilane are run in over the course of 6 hours 30 minutes, whilst keeping the reaction mixture at 80°C and distilling the dichlorosilane formed. A fraction weighing 75 g, containing 88.1% of dichlorosilane, is obtained. 533 g of a mixture containing 73% of phenyltrichlorosilane remain in the flask.

EXAMPLE 4

253 g of diphenyldichlorosilane and 15 g of aluminium chloride obtained after exposing aluminium chloride to moist air for 15 minutes are placed in a flask. 404 g of trichlorosilane are then run in over the course of 6 hours, whilst keeping the reaction mixture at 80°C and distilling the dichlorosilane formed. A fraction weighing 82 g, containing 80.4% of dichlorosilane, is obtained. 567 g of a mixture containing 68% of phenyltrichlorosilane remain in the flask.

The aluminium chloride in this Example was replaced by an anhydrous aluminium chloride. It was then observed that no dichlorosilane was obtained, all the other working conditions being the same. This proves that it is necessary to add a co-catalyst.

EXAMPLE 5

380 g of diphenyldichlorosilane, 22.5 g of anhydrous aluminium chloride and 6.8 g of alumina containing 2.5% of water (specific surface area of the alumina : 133 m$^2$/g) are introduced into a flask; 615 g of trichlorosilane are run in over the course of 6 hours 30 minutes, whilst keeping the reaction mixture at 70°C and distilling the dichlorosilane formed. 112 g of a fraction containing 79.5% of dichlorosilane are obtained.

EXAMPLE 6

380 g of diphenyldichlorosilane, 22.5 g of anhydrous aluminium chloride and 2.3 g of anhydrous alumina (specific surface area : 0.1 m$^2$/g) are placed in a flask. 477 g of trichlorosilane are run in over the course of 6 hours 50 minutes, whilst keeping the reaction mixture at 70°C and distilling the dichlorosilane. A fraction weighing 76 g, containing 74% of dichlorosilane, is obtained. 370 g of phenyltrichlorosilane are obtained on distilling the mixture remaining in the flask.

EXAMPLE 7

380 g of diphenyldichlorosilane, 22.5 g of anhydrous aluminium chloride and 0.2 g of hydrated alumina (water content : 27%; specific surface area : 5.8 m$^2$/g) are introduced into a flask. 478 g of trichlorosilane are run in over the course of 7 hours, whilst keeping the reaction mixture at 70°C and distilling the dichlorosilane. A fraction weighing 77 g, containing 74% of dichlorosilane, is obtained. 362 g of phenyltrichlorosilane are obtained on distilling the mixture remaining in the flask.

EXAMPLE 8

380 g of diphenyldichlorosilane, 22.5 g of anhydrous aluminium chloride and 1.35 g of hydrated alumina (as described in Example 7) are introduced into a flask. 533 g of trichlorosilane are run in over the course of 7 hours 20 minutes, whilst keeping the reaction mixture at 70°C and distilling the dichlorosilane. A fraction weighing 87 g, containing 81.2% of dichlorosilane, is obtained.

EXAMPLE 9

380 g of diphenyldichlorosilane (in which 0.7 g of hydrogen chloride has been dissolved beforehand by bubbling in the gas) and 22.5 g of aluminium chloride are introduced into the flask. 80 cm$^3$ of trichlorosilane are run in, the mixture is heated to 70°C and then 477 g of trichlorosilane are introduced gradually over the course of 7 hours 30 minutes, whilst distilling the resulting dichlorosilane as it is formed. A distillate weighing 79 g, containing 60.8 g of dichlorosilane, is obtained. 356 g of phenyltrichlorosilane are obtained on distilling the mixture remaining in the flask.

We claim:

1. Process for the preparation of dichlorosilane and phenyltrichlorosilane, which comprises reacting trichlorosilane and diphenyldichlorosilane in the presence of aluminium chloride, as catalyst, and a small proportion of a co-catalyst which is selected from hydrochloric acid and alumina and mixtures thereof, isolating the dichlorosilane from the reaction medium as it is formed and isolating the phenyltrichlorosilane obtained at the end of the reaction.

2. Process according to claim 1, in which the aluminium chloride is used in an amount, by weight, from 0.1 to 10% relative to the weight of the chlorosilanes employed.

3. Process according to claim 1, in which the co-catalyst is hydrochloric acid in an amount, by weight, of at most 30% of the weight of the aluminium chloride.

4. Process according to claim 3, in which the hydrochloric acid is used in an amount, by weight, of 0.1 to 10% of the weight of the aluminium chloride.

5. Process according to claim 1, in which the hydrochloric acid is formed in the reaction medium by adding water in the liquid state or in the vapour state to the reaction medium.

6. Process according to claim 1, in which the co-catalyst is alumina in an amount, by weight, of at most 20% of the weight of the chlorosilanes employed.

7. Process according to claim 6, in which the alumina is used in an amount, by weight, of 0.01 to 5% of the weight of the aluminium chloride.

8. Process according to claim 6, in which the co-catalyst is a hydrated alumina.

9. Process according to claim 1, which is carried out at 50° to 120°C.

* * * * *